United States Patent
Wang et al.

Patent No.: US 6,673,053 B2
Date of Patent: Jan. 6, 2004

(54) HYDROPHILIC LUBRICITY COATING FOR MEDICAL DEVICES COMPRISING AN ANTIBLOCK AGENT

(75) Inventors: Lixiao Wang, Maple Grove, MN (US); Irina Nazarova, Woodbury, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 76 days.

(21) Appl. No.: 09/307,309

(22) Filed: May 7, 1999

(65) Prior Publication Data

US 2002/0016574 A1 Feb. 7, 2002

(51) Int. Cl.[7] ............................................... A61M 5/32
(52) U.S. Cl. ...................................... 604/265; 604/172
(58) Field of Search ............................. 604/96.01, 264, 604/265, 523, 172; 606/191–192; 428/423.7, 447, 423.1; 427/2.22, 2.25, 336, 397; 424/424, 426

(56) References Cited

U.S. PATENT DOCUMENTS

| | | | |
|---|---|---|---|
| 2,814,296 A | 11/1957 | Everett | 128/339 |
| 3,566,874 A | 3/1971 | Sheperd et al. | 128/349 |
| 3,826,674 A | 7/1974 | Schwarz | 117/62.2 |
| 4,026,296 A | 5/1977 | Stoy et al. | 128/349 |
| 4,100,309 A | 7/1978 | Micklus et al. | 427/2 |
| 4,248,685 A | 2/1981 | Beede et al. | 204/159 |
| 4,373,009 A | 2/1983 | Winn | 428/424 |
| 4,447,590 A | 5/1984 | Szycher | 528/76 |
| 4,459,318 A | 7/1984 | Hyans | 427/36 |
| 4,465,738 A * | 8/1984 | Chang | 428/426 |
| 4,490,421 A | 12/1984 | Levy | 428/35 |
| 4,588,398 A | 5/1986 | Daugherty et al. | 604/265 |
| 4,876,126 A | 10/1989 | Takemura et al. | 428/35.7 |
| 4,921,483 A | 5/1990 | Wijay et al. | 604/96 |
| 5,041,100 A | 8/1991 | Rowland et al. | 604/265 |
| 5,084,315 A | 1/1992 | Karimi et al. | 428/36.6 |
| 5,091,205 A * | 2/1992 | Fan | 427/2 |
| 5,100,381 A | 3/1992 | Burns | 604/96 |
| 5,135,516 A | 8/1992 | Sahatjian et al. | 604/265 |
| 5,229,211 A | 7/1993 | Murayama et al. | 428/424.4 |
| 5,348,538 A | 9/1994 | Wang et al. | 604/96 |
| 5,441,488 A | 8/1995 | Shimura et al. | 604/265 |
| 5,490,839 A | 2/1996 | Wang et al. | 604/96 |
| 5,503,631 A | 4/1996 | Onishi et al. | 604/96 |
| 5,509,899 A * | 4/1996 | Fan et al. | |
| 5,531,715 A | 7/1996 | Engelson et al. | 604/265 |
| 5,556,383 A | 9/1996 | Wang et al. | 604/96 |
| 5,645,931 A | 7/1997 | Fan et al. | 428/334 |
| 5,670,558 A | 9/1997 | Onishi et al. | 523/112 |
| 5,693,034 A | 12/1997 | Buscemi et al. | 604/265 |
| 5,749,837 A | 5/1998 | Palermo et al. | 600/585 |
| 5,792,415 A | 8/1998 | Hijlkema | 264/530 |
| 5,849,209 A | 12/1998 | Kindt-Larsen et al. | 249/134 |
| 6,046,143 A | 4/2000 | Khan et al. | 508/208 |

FOREIGN PATENT DOCUMENTS

| | | |
|---|---|---|
| EP | 0 380 102 | 8/1990 |
| EP | 0 480 809 A2 | 4/1992 |
| EP | 0 519 604 A2 | 12/1992 |
| EP | 0 693 293 | 1/1996 |
| EP | 0 761 243 A1 | 3/1997 |
| WO | 91/08790 | 6/1991 |
| WO | 94/27665 | 12/1994 |
| WO | 98/58690 | 12/1998 |

OTHER PUBLICATIONS

Tecoflex® product literature.
M. Szycher, :Blood Compatible Materials and Devices Perspectives Towards the 21st Century, C.P. Sharma and M. Szycher eds.

* cited by examiner

Primary Examiner—Brian L. Casler
Assistant Examiner—Catherine Serke
(74) Attorney, Agent, or Firm—Vidas, Arrett & Steinkraus

(57) ABSTRACT

The present invention relates to a medical device for insertion into the body wherein said device has at least one surface which periodically comes into contact with a second surface, the first surface comprising a lubricious hydrophilic coating disposed thereon, said hydrophilic coating further comprising at least one antiblock agent.

21 Claims, 3 Drawing Sheets

HYDROPHILIC LUBRICITY COATING FOR MEDICAL DEVICES COMPRISING AN ANTIBLOCK AGENT

FIELD OF THE INVENTION

This invention relates to an improved hydrophilic coating for insertable or implantable medical devices comprising an antiblock agent.

BACKGROUND OF THE INVENTION

Water soluble, biocompatible compounds that impart lubricity to the surface of otherwise non-lubricious materials are desirable for use on medical devices which are inserted or implanted into the body. Such medical devices may include catheters that are utilized to deliver a stent, stent-graft, graft or vena cava filter, balloon catheters, other expandable medical devices and so forth. The industry has turned to hydrophilic lubricious coatings in order to overcome problems with commonly used hydrophobic coatings such as silicone, glycerine or olive oil.

Hydrophobic coatings, like silicone, have been known to wash off when exposed to an aqueous environment, lose initial lubricity rapidly, and lack abrasion resistance. Residual amounts of silicone have also been known to cause tissue reaction and irritation in patients. The loss of lubricity can lead to discomfort during insertion into a patient, and damage to blood vessels and tissues due to frictional forces during insertion or removal of the device.

Hydrophilic compounds that are biocompatible or blood compatible are more readily discharged from the body and have less of a tendency to cause tissue irritation.

One class of polymeric substances that dissolve or swell in an aqueous environment, often referred to as "hydrogels," are capable of manifesting lubricity while in a wet state, and are popularly utilized as lubricious coatings for medical devices. When hydrated, these substances have low frictional forces in humoral fluids including saliva, digestive fluids and blood, as well as in saline solution and water. Such substances include polyethylene oxides (optionally linked to the substrate surface by interpenetrating network, IPN, with poly(meth)acrylate polymers or copolymers; copolymers of maleic anhydride; (meth)acrylamide polymers and copolymers; (meth)acrylic acid copolymers; poly(vinyl pyrrolidone) and blends or interpolymers with polyurethanes; and polysaccharides.

These water soluble coating materials, while popular because they provide excellent lubricity and biocompatibility, may be sensitive to moisture.

A problem associated with the moisture sensitivity of such hydrogels is that they may prematurely uptake ambient moisture and become sticky or tacky. This results in what is referred to in the industry as a "self adhesion" effect. This can result in undesirable adhesion of the medical device to itself via the coating, to other devices, or to any other surface to which it comes in contact during sterilization or storage. In the case of dilatation balloons, after sterilization or storage hydrogel coatings on the folded section of the balloon can stick to themselves. This will lead to pinhole failure upon expansion of the balloon.

Metal wires, such as guide wires, may be coiled. The "self adhesion" effect can lead to removal of some of the coating or to failure of the coating from the surface of the wire as it is uncoiled.

These problems are discussed in U.S. Pat. No. 5,509,899 issued Apr. 23, 1996 to Fan et al. Fan et al. teaches a medical balloon and catheter which is wrapped and folded upon itself and in which the balloon is free of bridging and adhesion between abutting surfaces. The balloon has a base of a continuous polymeric surface which is expandable. On the polymeric surface is disposed a lubricious, biocompatible hydrogel coating and a thin, lubricious, blood-compatible coating is disposed on the hydrogel coating and adheres to it to prevent abutting surfaces of the folded polymeric surfaces from adhering to each other during inflation and to prevent delamination of the hydrogel coating and/or rupture of the balloon. Preferably, the blood-compatible coating is polyethylene glycol, methoxy polyethylene glycol or mixtures thereof having a molecular weight of between about 100 and 20,000. The blood-compatible coating is applied as an anti-blocking agent. See column 2 lines 18 to 37. However, application of a second coating can be costly.

The present inventors have found a hydrophilic, biocompatible coating for medical devices which avoids the aforementioned problems. The hydrophilic lubricious coating of the present invention comprises an antiblock additive which migrates to the surface of the coating, thereby impeding blocking or sticking of two surfaces and improving the performance of the medical device.

SUMMARY OF THE INVENTION

The present invent relates to medical devices which are designed for insertion or implantation into the body, and which device has at least one surface which periodically comes into contact with a second surface. The first surface is coated with a lubricious hydrophilic polymeric coating, and the coating also comprises at least one antiblock agent.

The antiblock agent blooms to the surface of the hydrophilic coating forming a protective layer on the surface to prevent self adhesion of the hydrophilic coating.

DETAILED DESCRIPTIONS OF THE PREFERRED EMBODIMENTS

Figure 1:
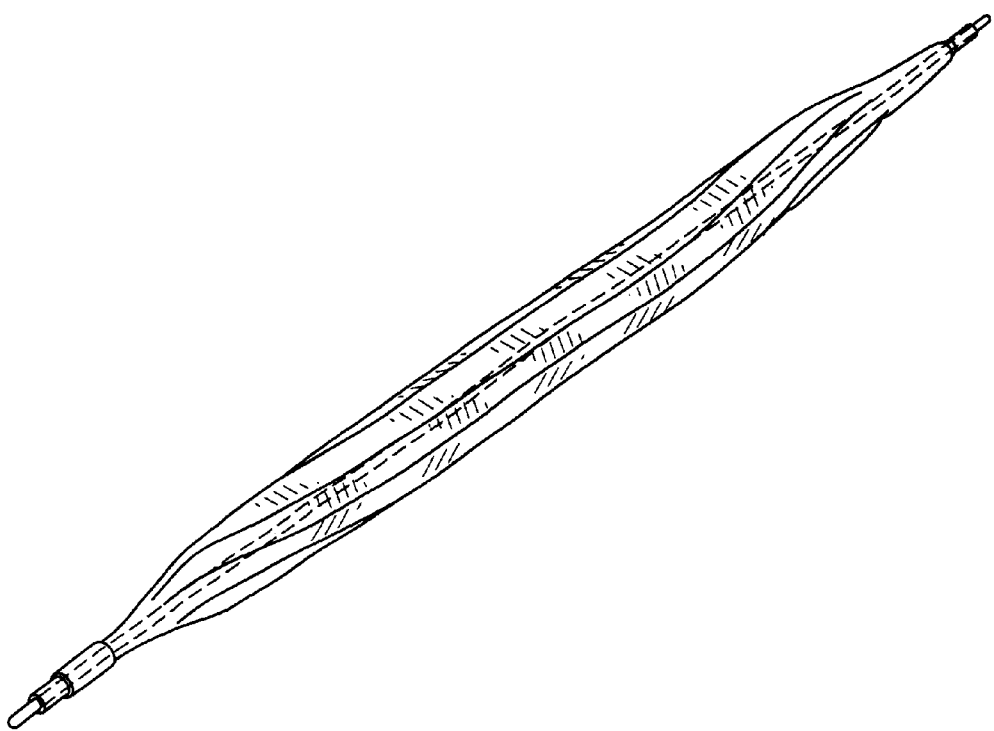
FIG. 1 is a side view of a catheter with a balloon tightly wrapped and folded for insertion for a medical procedure.
Figure 2:
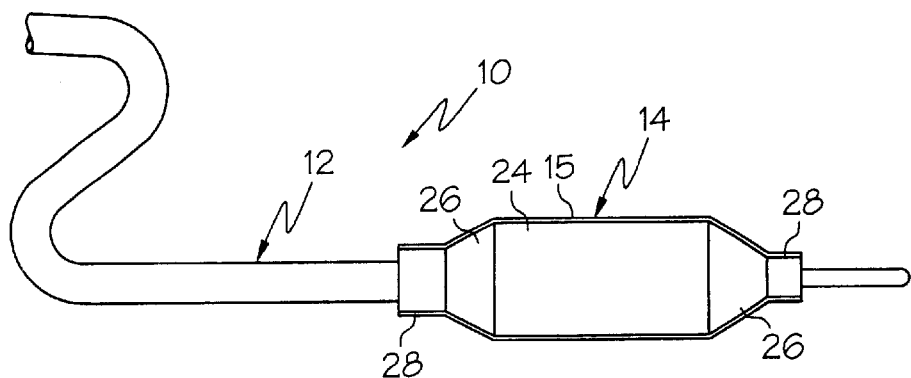
FIG. 2 is a perspective view of a dilatation catheter that includes the inflated coated balloon of FIG. 1.

FIG. 2 is a schematic representation of an inflated dilatation balloon catheter of the present invention, illustrated generally at 10. The inflated balloon 14 is mounted at the distal end of an elongated flexible shaft 12. Except as noted herein, catheter 10 is conventional in its construction, providing a lumen communicating with the interior of the balloon 14, for inflation and deflation of the balloon, and other optional features conventional in the dilatation catheter art. The balloon 10, has an inflated configuration, illustrated in FIG. 2 and is made up of three main portions: the body 24, the cones 26 and the waist portions 28. FIG. 1 illustrates the lubricious hydrogel coating 15, which comprises an antiblock agent, on the body 24, the cones 26 and the waist 28.

Balloons are typically made by a process by extruding the balloon material into a tubular preform, blow molding the balloon, and annealing. The tubular preform may be stretched prior to blowing.

Figure 3:
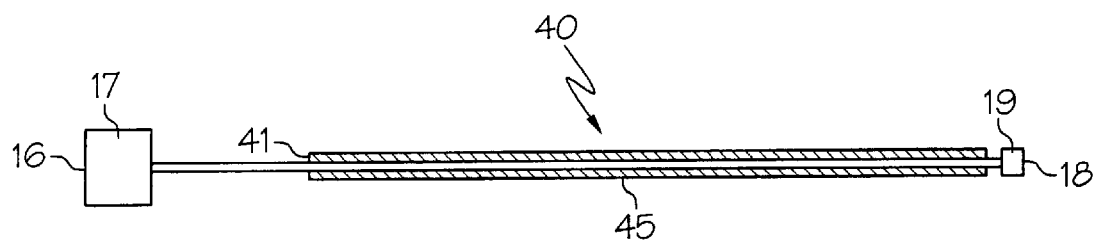
FIG. 3 is a schematic representation of an elongated medical device of the invention.

FIG. 3 is a schematic representation of an elongated medical device which may be a guide wire, catheter, cannula, fiber optic device and the like. Device 40 extends between proximal end 16 and distal end 18 and includes an elongate body 41. A control mechanism 17 may optionally be provided at or near the proximal end of device 40 to facilitate manipulation of the device and/or activation of functional structure provided on the device, such as drug delivery or balloon inflation lumen. Device 40 may also optionally be provided with a functional structure 19, such as an inflatable balloon, deployable stent, drug delivery mechanism, or the like, typically at or near the distal end 18.

Very little limitation is placed on the material for the elongate body 41. Most devices will have a relatively flexible body, such as when the device 40 is a catheter or guide wire. However, the invention may also be used with inflexible transcutaneous devices such as a needle. Body 41 may be made of organic high polymer materials such as polyamide, polyester, polyvinyl chloride, polystyrene, polyacrylate, polymethacrylate, polyacrylonitrile, polyacrylamide, polyethylene, polypropylene, polyurethane, polyvinyl acetate, silicone resins and copolymers and blends thereof. However, various inorganic materials such as glass, ceramic, stainless steel, and super elastic metal or shape memory alloy such as Ni—Ti, and the like may be employed on part or all of body 41. Body 41 may also be formed as a composite of different materials which are laminated together. Depending on the nature of the specific device 40, body 41 may be provided with one or more lumens, electrical connectors, optical fibers or the like, as is well known in the medical art.

One specific embodiment of device 40 is a balloon catheter for angioplasty and the like, in which case functional structure 19 will include an inflatable balloon, located very near the distal end 18 of device 40. The elongate body 41 will be a flexible tube, typically polymeric, containing at least an inflation fluid lumen for the balloon and a control mechanism 17 located at the proximal end 16 of device 40 of conventional design will be provided for manipulating the catheter to the desired site in the body and for causing the balloon to inflate and deflate as desired. Such a catheter may also be provided with a soft distal tip as part of functional structure 19 to facilitate maneuvering the balloon to cross a lesion and/or a guide wire lumen to allow the catheter to be inserted over a guide wire.

Another specific embodiment of device 40 is a guide wire in which case body 41 may be a metal wire. There may not be any control mechanism 17 present at the proximal end 16 and the distal functional structure 19 at the distal end 18 may simply be a conventional coiled or soft polymeric tip.

The coated portions may be body 41 of device 40 which is coated in FIG. 3 with a hydrophilic coating 45 comprising an antiblock agent.

If the functional structure 19 is a dilatation balloon, the balloon may also be coated as shown generally at 10 in FIG. 2 wherein the inflated balloon is coated with hyrogel coating 13 comprising an antiblock agent.

Figure 4:
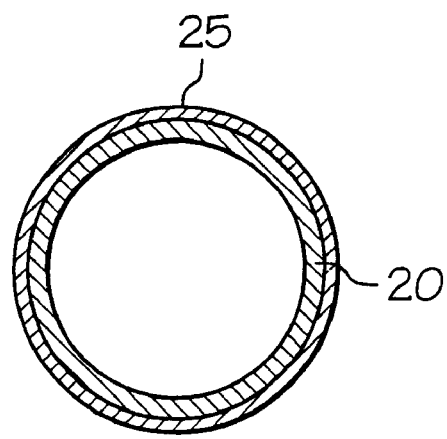
FIG. 4 is an enlarged cross-sectional view of the coatings as viewed on either the balloon of FIG. 2 or on an elongated medical device as in FIG. 3.

FIG. 4 is a schematic cross-sectional representation of a balloon wall 20 having a lubricious hydrophilic coating 25 comprising an antiblock agent disposed thereon. The wall may be formed from any flexible polymeric substance. In some preferred embodiments the balloon wall if formed from polyether block amides, such as Pebax® 7033 or 7233; polyester block ethers such as Arinitel® EM 40; polyethylene terephthalate; and nylon. FIG. 4 may also be representative of a coated tubular preform or an inner lumen for carrying fluids.

Figure 5:
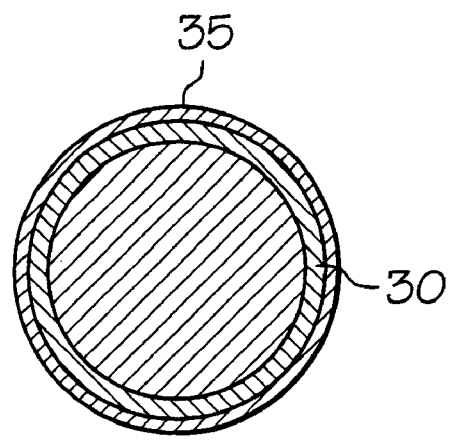
FIG. 5 is a schematic cross-sectional representation of a guide wire having a lubricious hydrophilic coating, the coating comprising an antiblock agent, disposed thereon.

FIG. 5 is a schematic cross-sectional representation of a guide wire 30 having a lubricious hydrophilic coating 35 comprising an antiblock agent disposed thereon.

FIG. 4 and FIG. 5 are expanded views of such medical devices and are not meant to limit the coat weight of the hydrogel coating.

The hydrogel coating has a thickness between about 0.2 and 10 $\mu$m, preferably 0.5 to 4 $\mu$m. The hydrogel coating is a lubricious, hydrophilic material which has the ability to dissolve or swell upon exposure to an aqueous type of environment. Water soluble polymers can be used which are generally chain-structured, non-crosslinked polymers having a hydrophilic group such as —OH, —CONH$_2$, —COOH, —NH$_2$, —COO—, SO$_3$, AND NR$_3^+$, where R is alkyl or hydrogen.

Natural water soluble polymers may also be utilized such as carboxymethyl cellulose, methyl cellulose, hydroxyethyl cellulose and hydroxypropyl cellulose, heparin, dextran, modified dextran and chondroitin sulphate.

Synthetic water soluble polymers include the polyalkylene glycols and polyoxyalkylene glycols such as polyethylene oxide, polyethylene oxide/polypropylene oxide copolymers and methoxypolyethylene oxide; copolymers of maleic anhydride including methyl vinyl ether-maleic anhydride copolymers; pyrrolidones including poly (vinylpyrrolidone); acryl amides including poly(N-alkylacrylamide); poly(acrylic acid); poly(carboxylic acids); poly(vinyl alcohol); poly(ethyleneimine); water soluble nylons; polyurethanes; and so forth.

Derivatives of any of these polymers may be utilized providing that enough of the basic structure of the polymers above that provides water sensitivity, solubility or dispersibility is retained allowing the polymer to uptake enough water to swell or partially dissolve enough upon exposure to moisture to provide lubricity in such a way to reduce frictional forces between the surface it is coated on and another surface such as tissue, metal or polymeric surfaces. Water insoluble derivatives may be employed as long as they have the freedom in the molecular chain and can be hydrated. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above-mentioned water soluble polymers. Also used are polymers crosslinked with substances having more than one reactive functional group such as diazonium, azide, isocyanate, acid chloride, acid anhydride, imino carbonate, amino, carboxyl, epoxy, hydroxyl, and aldehyde groups.

Copolymers with vinyl groups, acrylic acid, methacrylic acid, diene compounds and maleic anhydride have been preferably utilized.

In a particular preferred embodiment of the present invention, the hydrophilic coating is based on a maleic anhydride copolymer. Examples of such copolymers include poly(ethylene-maleic anhydride) sold by Aldrich Chemical Co. maleic anhydride-methyl vinyl ether copolymers such as Gantrez® AN 169 sold by G. A. F. Corporation.

Carboxylic acid-containing polymers may be preferably used as coating materials in the invention. Copolymers of acrylic acid, methacrylic acid, maleic acid, fumaric acid or other polymerizable ethylenically unsaturated acids are examples. These compounds may optionally be neutralized.

In another preferred embodiment, a hydrogel of polyethylene oxide may be captured in an interpenetrating crosslinked acrylic polymer network by polymerizing a mixture of an acrylic monomer composition comprising a monomer having plural (meth)acrylate groups and polyethylene oxide, thereby providing a hydrogel coating.

Other preferred hydrophilic coatings include polyethylene oxides, polyacrylic acid and polyvinylpyrrolidone.

The hydrophilic polymers of the present invention may be utilized in any combination to more narrowly tailor the resultant composition to the application. Some of the hydrophilic polymers of the present invention exhibit less flexibility than others. For instance, the flexibility of the hydrogels found in the previous paragraph above, may be improved by the addition of polyethylene oxide/polypropylene oxide copolymers, especially block copolymers, polyvinyl pyrrolidone, polyvinyl alcohol, and so forth.

The present invention contemplates the use of slip additives or antiblock agents to the hydrophilic coatings of the present invention. These compounds bloom to the surface of the hydrophilic coating, creating a protective outer layer which inhibits the premature uptake or absorption of ambient moisture by the hydrophilic coating, thereby preventing the coating from becoming tacky or sticky, and ultimately self adhering. The self adhesion of the coating can lead to pinhole formation in the balloon, or removal of the coating from the medical device itself. This in turn can lead to a number of problems including uncomfortable or painful insertion of the device into the body, rupture of dilatation balloons, high frictional forces between two surfaces leading to tissue damage or difficulty in manipulation of the device into the body, and so forth. If the device is difficult to manipulate, it can ultimately lead to misplacement of the device into the body therefore missing the target site.

There is a large variety of antiblock or slip additives that may be utilized in the present invention including anionic (negative charge), cationic (positive charge), nonionic (neutral) and amphoteric (have both anionic and cationic functionality) surfactants. Nonionic or neutral surfactants typically have a long tail which is often a long chain hydrocarbon, and a polar head. An example of one such class of surfactants is the fatty acid amides.

Examples of useful surfactants include long chain alkyl derivatives of fatty esters, fatty amides, fatty acid amides, fatty acids such as stearic acid or Crod Acid®, fatty amines, alcohols, fatty acid alcohols; phosphate esters of fatty alcohols; glycol ethers; fatty alcohol glycol ethers (fatty alcohol polyethylene/polypropylene glycol ethers) and so forth.

Waxes including polyethylene waxes, polypropylene waxes, oxidized waxes, and so forth may also be useful to the present invention. More specifically included are polyethylene waxes such as Epolene® waxes from Eastman Chemical Co. in Kingsport, Tenn.; ethylene-bis-stearamide waxes; glycerol monostearates, fatty amide waxes such as the Kemamide® amides series from Witco or the Mold Pro® amides from Humko; metallic stearates, Montan® mineral wax; and so forth.

More specifically, the silicones useful herein include those materials having silicon oxygen polymer backbones with carbon containing side chains of hydrocarbyl groups containing 1–6 carbon atoms. More specifically, the polymer consists of a structure consisting of alternate oxygen and silicon atoms. Included in this group are silicone oils, silicone wax (steroyldimethicone), dimethyl silicones and so forth. Specific examples include those available under the tradename of Abilwax® and those available from Dow Corning® such as 200, 203 and 230 and the Kantstick® series of silicones. Polydimethylsiloxane with grafted polyether groups (polyethylene oxide/polypropylene oxide) is an amphoteric surfactant available from Witco under the tradename of Silvet® L-7657 and is found in one embodiment of the present invention.

The amide waxes preferably have up to 40 carbon atoms and include the higher fatty acid amides which have an uneven number of carbon atoms. These include These include the Crodamide® series of fatty acid amides available from Croda International Plc Oleochemicals and Polymer Additives Division; the Kemamide® B, S, and U, ethylene bis (stearamide), oleamide and erucamide fatty amides available from Witco; Paricin® 220 and 285 stearamide waxes available from Caschem; the Petrac® series; Acrawax®C, an ethylene bis stearamide (also referred to as ethanediylbiscoctadecanamide) available from Lonza; Adwax® 280; Rosswax® 140; and so forth. These fatty acid amides will orient themselves on the surface of the coating.

Examples of polyethylene waxes include the Epolene® C series available from Eastman Chemical Co. in Kingsport, Tenn. as well as some of the Epolene® E and N series including C-10, C-13, C-14, C-15, C-17, C-18, E-10, N-10, N-11, N-21 and N-34. Eastman Chemical Co. also has polypropylene waxes available under the Epolene® tradename such as N-15P and E-43P. Hoechst Celanese in Germany manufacturers polyethylene waxes under the tradename of Hoechst Wax.

Oxidized waxes are alkane hydrocarbons capped with either ester, carboxylic or hydroxy groups. Oxidized homopolymers are available from Allied Signal under the tradename of A-C®. Other oxidized waxes include carnauba wax such as Kantstik® wax available from Specialty Products Co., Evergreen Product line, and Rosswax®.

Glycerol esters are useful to the present invention including monoglycerides, diglycerides and polyglycerides including fatty acids of triglycerides, and so forth. These are available under the tradename of Pationic® from Patco Polymer Additives in Kansas City, Mo. Such products include glycerol monostearates 900, 901, 902, 905 and 909; glycerol monooleate 907; glycerol tristearate 919; and mono/diglycerides 1042 and 1042K.

Alcohol esters having 5–2000 carbon atoms are useful to the present invention. Copolymers of organic phosphate esters, also referred to as complex esters, which also may contain glycerides, organic acid derivatives and having acids, and having molecular weights of about 200–2000 g/mole are also useful to the present invention. These include the Kantstik® series of release agents, such as FX-9, Q, S and so forth, available from Specialty Products Co., Evergreen Products line.

Anionic surfactants, or those carrying a negative charge, include sulfonate based surfactants such as Bio-Terge® AS-40, a sodium salt of α-olefin sulfonate available from the Stepan Co. and Rhodacal® LDS 22, a sodium salt of dodecylbenzene sulfonate available from Rhodia, Inc.

Cationic surfactants, those carrying a positive charge, include amine salts such as Schercopol® DS-140 available from Scher Chemicals.

Amphoteric surfactants are those which have both anionic and cationic functionality on the same molecule. An example of an amphoteric surfactant is polydimethylsiloxane with grafted polyether groups (polyethylene oxide/polypropylene oxide), Silvet® L-7657 supplied by Witco.

These are only a few illustrations of antiblock agents available and this is not intended as a comprehensive list. The antiblock agent will be selected based on the compatibility with the hydrophilic coating. The antiblock agent should be just incompatible enough that it will bloom to the surface of the hydrophilic coating, once the coating is dried, but should not phase separate while in solution. The antiblock agent is useful at a concentration from about 1 to about 20% by weight in solution, preferably from about 5% to about 10% by weight.

The antiblock agents are dissolved, along with the hydrophilic coating in a solvent or a mixture of solvents. Useful solvents include alcohols, aliphatic hydrocarbons, aromatic hydrocarbons, chlorinated solvents, esters, glycols, glycol ethers, ketones, and so forth. Polar solvents include alcohols, glycols, water and so forth. Specific examples include ethanol, methanol, isopropyl alcohol (IPA), stearyl alcohol, ethylene glycol, propylene glycol, glycerin, water, methylethyl ketone (MEK) and so forth. Non-polar solvents include aliphatic hydrocarbons such as heptane and hexane; aromatic hydrocarbons such as toluene and xylene; chlorinated hydrocarbons such as perchloroethylene, methylene chloride, chloroform, carbon tetrachloride, 1,1,1-trichloroethane; fluorocarbons; mineral spirits and so forth.

The coating compositions of the present invention are coated out of a solvent or a cosolvent mixture using any conventional coating techniques such as dipping of the medical device into the coating solution, spraying the article, brushing the coating on, and so forth.

The solvent will then evaporate and the coating will become dry on the surface of the coated medical device. The slip additive or antiblock agent typically migrate or "bloom" to the surface once the coating has lost most or all of the solvent. This antiblock agent thus forms a protective coating over the surface of the hydrophilic lubricious coating, preventing the premature absorption of too much moisture. If too much moisture is absorbed by the hydrophilic polymer, it becomes sticky and tacky and will stick to itself or bridge.

The following non-limiting examples further illustrate the coatings of the present invention.

EXAMPLES

Example 1

A solution of an anionic surfactant, Bio-Terge®AS-40, a sodium salt of L-olefin sulfonate sold by the Stepan Company, at a 10% concentration in saline, was mixed with a hydrophilic coating solution of a polyethylene oxide (molecular weight 900,000 g/mole) in a cosolvent mixture of water and IPA wherein the polyethylene oxide is at 2% concentration. The mixture was done in a 1:4 anionic surfactant solution to hydrophilic coating solution based on solids content.

Pebax® films were coated with a control sample of hydrophilic coating solution which contained no antiblock agent, as well as the mixture noted above. The coatings were dried and overlap coupons were prepared. Samples were sterilized using ethylene oxide gas at 45° C. and relative humidity of 50% for 13 hours.

Shear forces were tested on a 1"×0.5" specimen using an Instron at a load of 20 lbs (9.07 kg). The hydrophilic coating without the antiblock agent exhibited a shear value of 19.98 lbs (9.06 kg) while the coating with the antiblock agent exhibited a shear value of 3.5–4.5 lbs (1.59 kg–2.04 kg). The self adhesion effect was therefore reduced by 5 times.

Example 2

A 10% solution of a cationic surfactant, a mix of amine salts sold under the tradename of Schercopol® DS-140 supplied by Scher Chemicals, Inc. in water was mixed with a 5% solution of hydrophilic coating, polyvinylpyrrolidone, in a water/IPA cosolvent mix at a ratio of 1:5 based on solids content. Pebax® films were coated with both a control and with the mixture herein following the same procedure in Example 1 above. Instron testing was completed and a significant shear force reduction was noted.

Example 3

A 5% solution of polyethylene glycol, Carbowax® 8000 Sentry Grade supplied by Union Carbide (m.w.=8000 g/mole) in water/IPA wax mixed with a 5% solution of a hydrophilic coating, polyacrylic acid, in water/IPA at a ratio of 1:5 based on solids content. Arnitel® films were coated with a control solution of the hydrophilic coating without antiblock agent and with the mixture herein. The dried overlap coupons were prepared and tested on the Instron as in Example 1. A significant shear force reduction was noted between the coating with no antiblock agent and the coating with antiblock agent.

Example 4

A 5% solution of an amphoteric surfactant, polydimethylsiloxane with grafted polyether groups (polyethylene oxide/polypropylene oxide), Silvet® L-7657 supplied by Witco, was mixed with an 8% solution of a hydrophilic coating, polyethylene maleic acid copolymer in MEK/IPA in a ratio of 1:10 based on solids content. Nylon® 6 films were coated with both a control of the hydrophilic coating without antiblock agent and with the mixture herein. The procedure as in Example 1 was followed. The shear force reduction between the control and the coating with antiblock agent was significant.

Example 5

A 10% solution of an anionic surfactant, dodecylbenzene sulfonate sodium salt, Rhodacal® LDS 22 supplied by Rhodia Inc. in water was mixed with a 2% solution of a hydrophilic coating, polyethylene oxide, in water/IPA in a ratio of 1:5 based on solids content. Pebax® films were coated with both a control solution of the hydrophilic coating without antiblock agent and with the mixture herein. The same procedure as in Example 1 was followed. Shear force reduction between the control sample and the hydrophilic coating with the antiblock agent was significant.

What is claimed is:

1. A medical device for insertion into the body, said device having at least one first surface which periodically comes into contact with a second surface, said first surface having a lubricious hydrophilic single layer coating disposed thereon, said hydrophilic single layer coating comprising an antiblock agent which blooms toward the surface of said hydrophilic coating.

2. A medical device for insertion into the body, said device having at least one surface which periodically comes into contact with a second surface, said first surface comprising a lubricious hydrophilic top coating disposed on said first surface wherein said hydrophilic top coating comprises at least one polymeric material selected from the group consisting of polyalkylene glycols, alkoxy polyalkylene glycols, copolymers of methylvinyl ether and maleic acid poly (vinylpyrrolidone), poly(N-alkylacrylamide), poly(acrylic acid), poly(vinyl alcohol), poly(ethyleneimine), methyl cellulose, carboxymethyl cellulose, polyvinyl sulfonic acid, heparin, dextran, modified dextran and chondroitin sulphate and at least one antiblock agent.

3. A medical as in claim 1 wherein said antiblock agent is selected from the group consisting of long chain alkyl derivatives of fatty esters, fatty amides, fatty acid amides, fatty acids, fatty amines, fatty alcohols, fatty acid alcohols, polyalkylene waxes, oxidized polyalkylene waxes, silicone waxes, silicone oils, alphaolefin sulfonates, phosphate ester of fatty alcohols, and mixtures thereof.

4. The medical device of claim 3 wherein said antiblock agent is an oxidized polyalkylene wax.

5. The medical device of claim 4 wherein said oxidized polyalkylene wax is an alkane hydrocarbon capped with at least one functional group which is an ester, carboxyl, hydroxyl, or mixture thereof.

6. The medical device of claim 1 wherein said antiblock agent prevents premature absorption of water by said hydrophilic coating.

7. A method for producing a medical device as in claim 1 comprising the step of coating said device with a mixture comprising a lubricious hydrophilic polymeric material and said at least one antiblock agent.

8. The method of claim 7 wherein said method is selected from the group consisting of dipping, spraying, brushing and mixtures thereof.

9. The method of claim 8 wherein said method is accomplished out of a solvent selected from the group consisting of alcohols, chlorinated solvents, esters, glycols, glycol ethers, ketones, aliphatic hydrocarbons, aromatic hydrocarbons, and mixtures thereof.

10. The medical device of claim 1 wherein said antiblock agent is selected from the group consisting of long chain alkyl derivatives of fatty esters, fatty amides, fatty acid amides, fatty acids, fatty amines, alcohols, fatty acid alcohols, polyalkylene waxes, oxidized polyalkylene waxes, and mixtures thereof.

11. The medical device of claim 1 wherein said medical device is a dilatation balloon.

12. The medical device of claim 11 wherein said balloon comprises a polymeric material selected from the group consisting of polyether block amides, polyester block ethers, polyethylene terephthalate and nylon.

13. The medical device of claim 1 wherein said medical device is a guide wire.

14. The medical device of claim 1 wherein said hydrophilic coating comprises at least one polymer selected from the group consisting of copolymers of maleic anhydride and polycarboxylic acids.

15. The medical device of claim 1 wherein said antiblock agent is a surfactant.

16. The medical device of claim 15 wherein said surfactant is selected from the group consisting of cationic, anionic, amphoteric and mixtures thereof.

17. The medical device of claim 15 wherein said surfactant is nonionic.

18. The medical device of claim 15 wherein said surfactant is a member selected from the group consisting of ethylene oxide/propylene oxide modified polydimethylsiloxane block copolymers, anionic sulfonates, cationic amines, and mixtures thereof.

19. The medical device of claim 18 wherein said anionic sulfonate is an alpha olefin sulfonate, an alkylaryl sulfonate, or mixture thereof.

20. A medical device for insertion into the body, said device having at least one surface which periodically comes into contact with a second surface, said first surface comprising a lubricious hydrophilic coating disposed on said first surface wherein said hydrophilic coating comprises at least one hydrophilic polymer and at least one antiblock agent selected from long chain alkyl derivatives of fatty esters, fatty amides, fatty acid anides, fatty acids, fatty amines, alcohols, fatty acid alcohols, polyalkylene waxes, oxidized polyaylkylene waxes, silicone waxes, alphaolefin sulfonates, phosphate ester of fatty alcohols, and mixtures thereof.

21. A medical device for insertion into the body, said device having at least one surface which periodically comes into contact with a second surface, and said device having a coating which is a mixture of a hydrophilic coating and an antiblock agent applied to said first surface wherein said antiblock agent blooms toward the surface of said hydrophilic coating, said coating forming a single layer on said surface of said device.

* * * * *